(12) United States Patent
Hürland et al.

(10) Patent No.: US 6,716,336 B2
(45) Date of Patent: Apr. 6, 2004

(54) SENSOR FOR DETERMINING THE CONCENTRATION OF SULPHUR COMPOUNDS IN A LIQUID

(75) Inventors: Armin Hürland, Friedrichshafen (DE); Roland Kemmler, Stuttgart (DE); Ralf Moos, Friedrichshafen (DE); Carsten Plog, Markdorf (DE); Thomas Stengel, Friedrichshafen (DE); Dirk Voigtländer, Korntal-Münchingen (DE)

(73) Assignee: DaimlerChrysler AG, Stuttgart (DE)

( * ) Notice: Subject to any disclaimer, the term of this patent is extended or adjusted under 35 U.S.C. 154(b) by 39 days.

(21) Appl. No.: 09/953,193

(22) Filed: Sep. 17, 2001

(65) Prior Publication Data

US 2002/0079236 A1 Jun. 27, 2002

(30) Foreign Application Priority Data

Sep. 16, 2000 (DE) .......................... 100 45 939

(51) Int. Cl.[7] .............................. G01N 27/406
(52) U.S. Cl. ............... 205/786.5; 204/422; 204/426; 205/775
(58) Field of Search ................ 204/421–429; 205/786.5, 775

(56) References Cited

U.S. PATENT DOCUMENTS

| 3,821,090 | A | * | 6/1974 | Topol et al. |
| 4,188,266 | A | * | 2/1980 | Forman |
| 4,406,754 | A | * | 9/1983 | Narita et al. |
| 4,622,105 | A | * | 11/1986 | Liu et al. |
| 4,842,698 | A | * | 6/1989 | Kirchnerova et al. |
| 5,322,611 | A | * | 6/1994 | Zaromb |
| 5,656,143 | A | * | 8/1997 | Swetnam et al. |
| 5,707,502 | A | | 1/1998 | McCaffrey et al. |
| 5,770,028 | A | | 6/1998 | Maley et al. |
| 5,863,400 | A | | 1/1999 | Drummond et al. |
| 6,200,445 | B1 | * | 3/2001 | Yokota et al. |
| 6,365,022 | B1 | * | 4/2002 | Hitchman et al. |

FOREIGN PATENT DOCUMENTS

| DE | 198 13 654 | 9/1999 |
| DE | 198 45 397 | 4/2000 |
| EP | 0 631 130 | 12/1994 |
| EP | 0 858 837 | 8/1998 |
| EP | 0 860 595 | 8/1998 |
| EP | 0 899 430 | 3/1999 |
| JP | 63-311164 | 4/1989 |

OTHER PUBLICATIONS

W. Strehlau, et al., "New developments in lean NOx catalysis for gasoline fueled passenger cars in Europe", SAE–Paper 962047, (1996). Described in specification. Month unavailable.

Patent Abstracts of Japan vol. 013, No. 149 (P–855), Apr. 12, 1989 (Apr.–12–1989) & Database WPI Section Ch, Week 198905 Derwent Publications Ltd., London, GB; Class E36, p. 4, AN 1989–036905.

* cited by examiner

*Primary Examiner*—T. Tung
(74) *Attorney, Agent, or Firm*—Kenyon & Kenyon

(57) ABSTRACT

A sensor for determining the concentration of sulphur compounds in a liquid includes: a working electrode in contact with the liquid to be analyzed; a referenced electrode insulated from the liquid to be analyzed; a liquid-impermeable membrane located between the working electrode and the reference electrode and permeable to an ion that may form a chemical compound with the sulphur compounds in the liquid to be analyzed; and a reference material in contact with the reference electrode or forms the reference electrode.

19 Claims, 7 Drawing Sheets

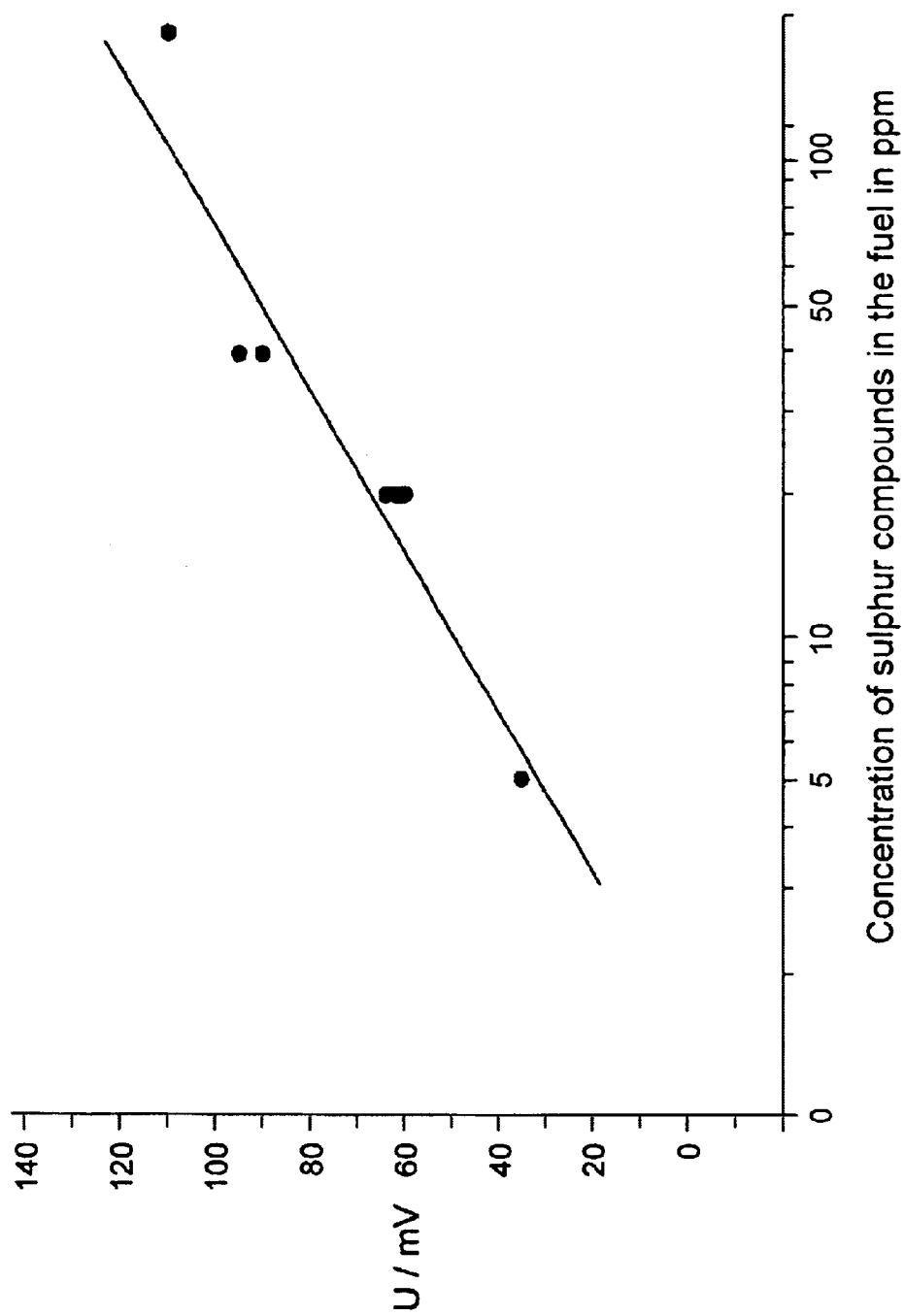
F I G. 3

SENSOR FOR DETERMINING THE CONCENTRATION OF SULPHUR COMPOUNDS IN A LIQUID

FIELD OF THE INVENTION

The invention relates to a sensor for detecting the concentration of sulphur compounds in a liquid.

BACKGROUND INFORMATION

The main emitters of nitrogen oxides (NOx) in industrial countries are transport, power stations fired by fossil fuels and industrial plants. While the emissions from power stations and industry are continuing to decrease, the proportion due to traffic is becoming ever more prominent.

The NOx emissions of petrol-powered 4-stroke engines can be drastically reduced by operation at an air ratio $\lambda=1$ and exhaust gas purification after the engine by a 3-way catalyst. In principle, this possibility does not exist in a mixture-regulated diesel engine which is operated superstoichometrically. Due to the high proportion of oxygen in the exhaust gas, no catalyst which can reduce the NOx emissions without the addition of reducing agents, e.g. hydrocarbons or ammonia-forming compounds, has been found.

The same applies to 4-stroke engines which are run lean. In that case, there have for some time been vehicles having an exhaust gas train provided with a catalyst which is run lean ($\lambda>1$) for a certain time and can store nitrogen oxides during this time. After this "storage phase" in which the catalyst is "charged" with the nitrogen oxides to be stored, there follows a generally much shorter desorption phase during which the catalyst is "emptied". During the desorption phase, the engine is run rich ($\lambda<1$). Strehlau W., Leyer J., Lox E. S., Kreuzer T., Hori M., Hoffmann M.: New developments in lean NOx catalysis for gasoline fueled passenger cars in Europe, SAE-Paper 962047 (1996) describes a catalyst which is suitable for such conditions. The expression "NOx trap" is also used in the literature.

The catalyst materials used for an NOx trap include, inter alia, alkali metal compounds or alkaline earth metal compounds which are responsible for storage of the nitrogen oxides. Unfortunately, such compounds react preferentially with sulphur oxides which are likewise present in the exhaust gas and are formed during combustion of the sulphur compounds (e.g., mercaptans, thiophenes, thioethers, thioesters, disulphides) present in the fuel and are converted into alkali metal or alkaline earth metal sulphates. For this reason, such storage catalysts lose their storage capability after a certain operating time which is dependant on the concentration of the sulphur compounds in the fuel. They have to be desulphated. Methods for desulphurising such storage catalysts are described, for example, in European Published Patent Application No. 0 858 837, European Published Patent Application No. 0 860 595, and European Published Patent Application No. 0 899 430. The engines are no longer run during the regeneration phase in the normal alternating lean/rich operation described above but are instead continually run rich and a certain minimum temperature required for desulphurisation has to be reached.

Since fuel consumption is significantly increased during such a desulphurisation phase because of running rich, desulphurisation should be carried out only when absolutely necessary. The optimum time for a desulphurisation phase can be determined as described in European Published Patent Application No. 0 860 595 by a functional relationship depending on the content of sulphur compounds in the fuel used, the current mass flow of fuel in the internal combustion engine and the current exhaust gas temperature at the "NOx trap", but the content of sulphur compounds in the fuel is usually unknown. However, there is at present no known sensor which would be suitable for determining the content of sulphur compounds in a fuel in a production vehicle.

To protect the NOx trap from sulphur compounds, German Published Patent Application No. 198 13 654 describes the installation of a construction containing a sulphur-storing compound upstream of the NOx trap so that all sulphur remains in the SOx trap and the function of the NOx trap is therefore not impaired. However, the SOx trap also has to be regenerated from time to time or, if its storage capacity is sufficiently large, replaced. Determination of the "degree of loading" of such an SOx trap requires a sulphur sensor so that the degree of loading can be derived from the values measured by the sensor using an integration method.

The degree of loading of a desulphurisation device for fuel, as described in German Published Patent Application No. 198 45 397, could also be determined using a sulphur sensor and an integration method.

The concentration of sulphur compounds in the fuel can be of interest not only in the case of a 4-stroke engine but also in the case of a diesel engine. This is particularly true when particular novel sulphursensitive NOx- or $NH_3$-storing catalysts are to be used for exhaust gas purification.

The concentration of sulphur compounds in methanol, which has been discussed as fuel for fuel cell vehicles, can also be of interest.

The concentration of sulphur compounds in other fuels such as ethanol or liquefied gas can also be of interest.

In addition, the concentration of sulphur compounds in fuel oil used for firing stationary facilities may be of interest.

It is an object of the present invention to provide a sensor for determining the concentration of sulphur compounds in a liquid, in particular a motor fuel, which is inexpensive to produce and has a small size so that it is suitable for use in production vehicles.

SUMMARY

The sensor according to the present invention for determining the concentration of sulphur compounds in a liquid includes:

- a working electrode in contact with the liquid to be analyzed;
- a reference electrode insulated from the liquid to be analyzed;
- a liquid-impermeable membrane which is located between the working electrode and the reference electrode and is permeable to an ion which may form a chemical compound with the sulphur compounds in the liquid to be analyzed; and
- a reference material which is in contact with the reference electrode or forms the latter.

The sulphur sensor according to the present invention is inexpensive to produce and is, due to its small size and lack of complexity, particularly suitable for use in a production vehicle.

It may be used, in particular, for determining the degree of sulphur charge of an NOx trap in the exhaust gas purification system of a 4-stroke engine which is run lean. All other applications described above are also possible for the sensor of the invention.

BRIEF DESCRIPTION OF THE DRAWINGS

FIG. 3 is a graph illustrating a characteristic line of the sensor illustrated in FIG. 1 of the output voltage of the sensor as a function of the concentration of sulphur compounds in the fuel.

DETAILED DESCRIPTION

Figure 1:
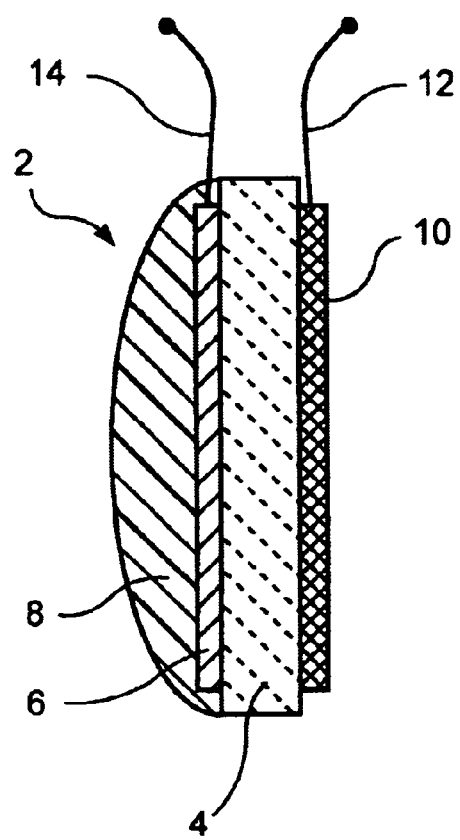
FIG. 1 illustrates a first example embodiment of a sensor according to the present invention.

FIG. 1 illustrates a first embodiment of the sensor 2 according to the present invention. A silver layer 6 is applied as reference electrode to one side of a liquid-impermeable membrane 4 which conducts silver ions. The layer 6 is provided with a liquid-tight covering, e.g., by a covering layer or, as illustrated in FIG. 1, a covering composition 8. A working electrode 10 including a, e.g., porous electrical conductor, which may contain no silver components and may be resistant to the liquid, is applied to the other flat side of the membrane 4. Both the electrode 10 and the silver layer 6 are provided with a lead 12 and 14. The sensor output voltage is measured between the leads 12 and 14. When the sensor 2 is dipped into a liquid, one side of the sensor is in contact with the liquid while the other side is not in contact with the liquid.

To construct the sensor illustrate in FIG. 1, it is possible to use, for example, the following materials: Ag-β"-Al$_2$O$_3$ for the membrane 4 which conducts silver ions, porous gold for the working electrode 10 and epoxy resin for the covering composition 8.

Figure 2:
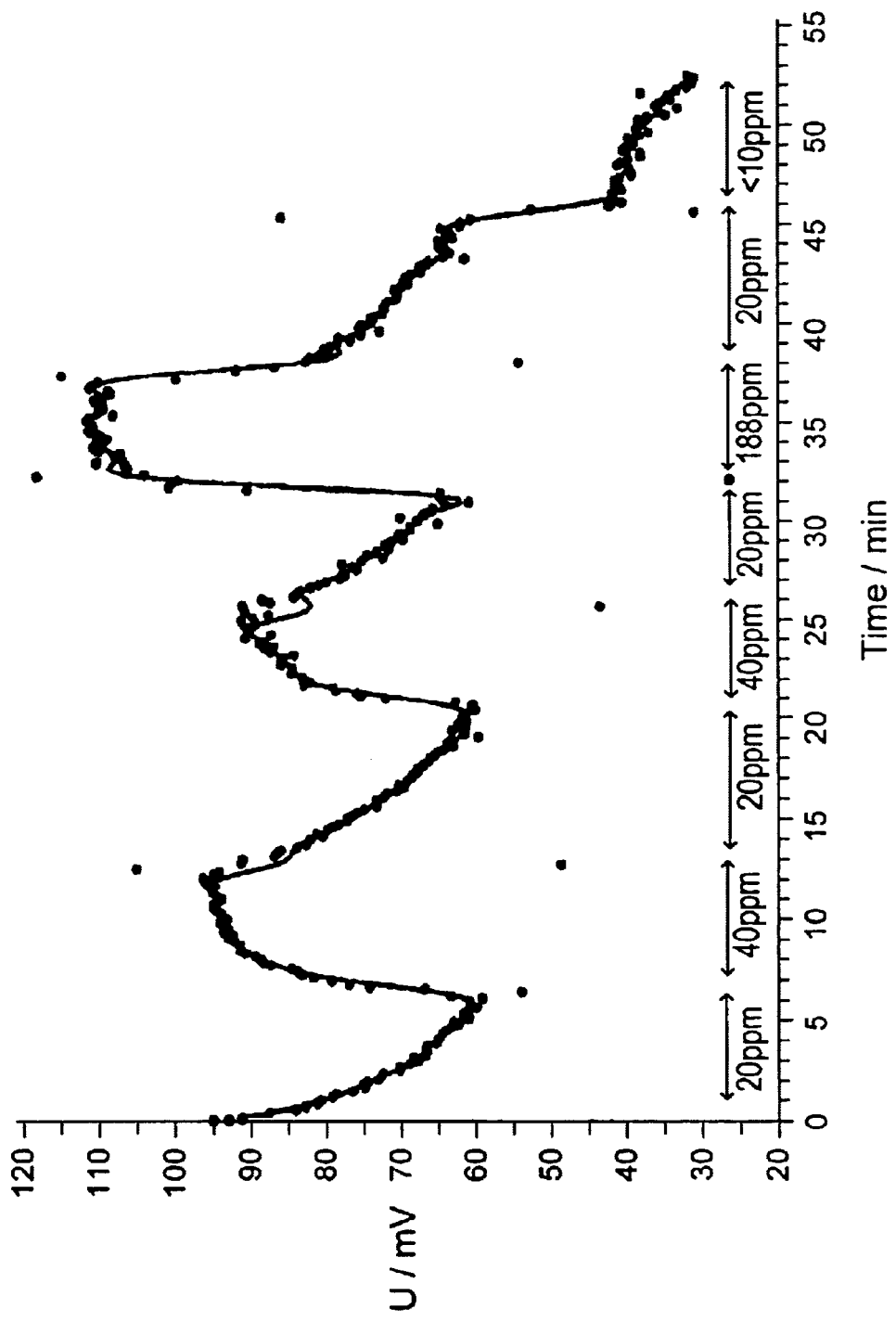
FIG. 2 is a graph illustrating a measured output voltage of the sensor illustrated in FIG. 1 that is exposed to petrol containing various concentrations of sulphur compounds.

FIG. 2 illustrates a typical recording of the signal from such a sensor. The dots represent individual measurements, and the continuous line is a smoothed representation. The sensor was firstly dipped into petrol, concentration of sulphur compounds of which was determined by analysis as 20 ppm. It was then dipped into grades of petrol having different concentrations of sulphur compounds; the reproducibility was tested first by dipping the sensor alternately in petrol containing 40 ppm and 20 ppm. It was then dipped into petrol containing 188 ppm and then again into petrol containing 20 ppm and subsequently into petrol having a concentration of sulphur compounds which was determined by analysis as less than 10 ppm. The sensor reacts to the sulphur content of the fuel. Since virtually constant final values were achieved, a characteristic line may be recorded for the sensor. FIG. 3 illustrates the characteristic line of the sensor illustrated in FIG. 2, i.e., the sensor output voltage versus the concentration of sulphur compounds in the fuel. In the semi-logarithmic plot, the measured values are approximately on a straight line having a gradient of 59.5 mV/(power of 10 of sulphur).

The mode of action may be understood as follows: the reaction of sulphur-containing compounds in the fuel with silver represents the half-cell reaction at the working electrode. The second half-cell reaction is the oxidation of silver to the silver ion at the reference electrode. Connection of the two electrodes by a conductor of silver ions results in generation of the Nernst potential, the magnitude of which serves as a measure of the concentration of sulphur compounds. A semilogarithmic plot is expected to be a straight line where the gradient is:

$$2.303 * k * T/e = 59.5 \ mV/(\text{power of 10 of sulphur}) \quad (1)$$

In this equation, k is the Boltzmann constant, e is the charge on the electron and T is the absolute temperature in kelvin. The factor 2.303 results from the conversion from the natural logarithm to the logarithm to the base 10.

Figure 4:
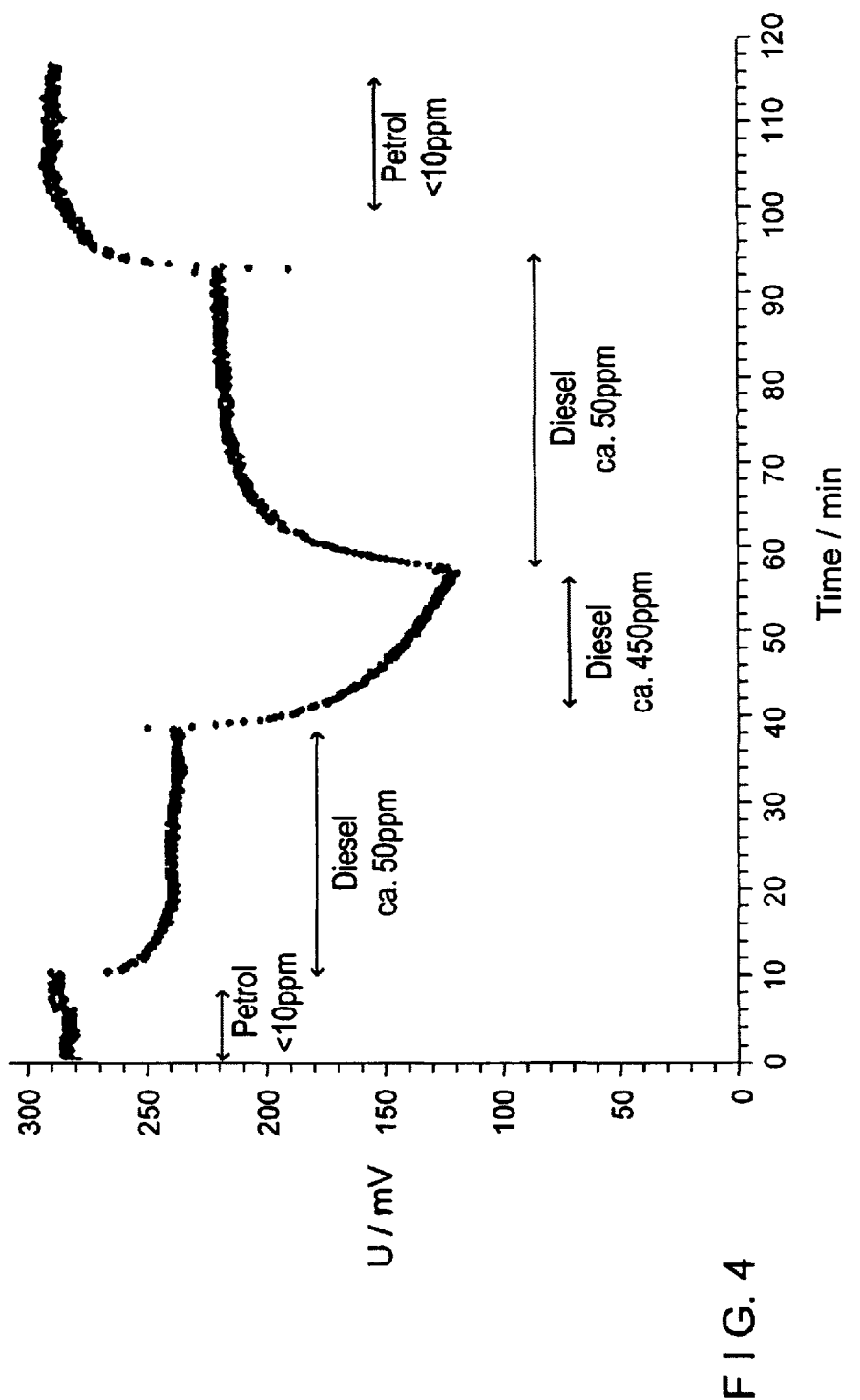
FIG. 4 is a graph illustrating a recording of the measured output voltage of the sensor illustrated in FIG. 1 that is exposed to various fuels containing various concentrations of sulphur compounds.

FIG. 4 is a recording of the measured output voltage of such a sensor when it is exposed to various fuels containing various concentrations of sulphur compounds. At the beginning, the sensor was dipped into petrol having an analytically determined concentration of sulphur compounds of less than 10 ppm. It was then dipped into conventional diesel containing about 50 ppm, subsequently into diesel containing about 450 ppm, subsequently into diesel containing about 50 ppm and finally once again into petrol having an analytically determined concentration of sulphur compounds of less than 10 ppm. The dependence of the sensor signal on the sulphur concentration and the reproducibility are illustrated. Compared with the recorded measurements illustrated in FIG. 3, the measurement was recorded at reversed polarity, so that the sensor signal decreases with increasing sulphur content.

The membrane 4 may be made of any ion conductor where the ions may form a chemical compound exclusively with the sulphur of the fuel. Silver ion conductors may be well suited. These may be inorganic materials such as Ag-β"Al$_2$O$_3$, Ag-β-Al$_2$O$_3$, AgCl, AgI or other compounds. However, it is also possible to use organic silver ion conductors, e.g., plastics which conduct silver ions. The ionic conductivity at the working temperature may be sufficiently high for the electric potential between the two leads 12 and 14 (FIG. 1) to be measured without problems.

Figure 5:
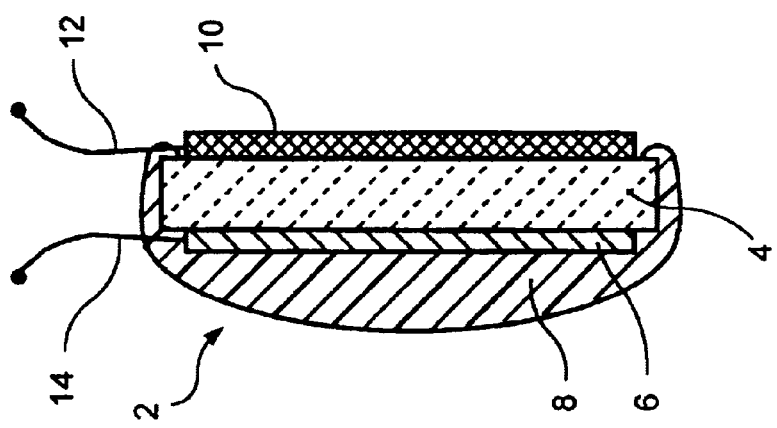

As illustrated in FIG. 5, the sensor component 2 may be constructed so that the covering composition 8 extends beyond the side edge as far as the front electrode, so that only the electrode 10 is in contact with the liquid to be analyzed. This has the advantage that the reaction with sulphur occurs exclusively at the three-phase boundary membrane/working electrode/liquid.

Figure 6:
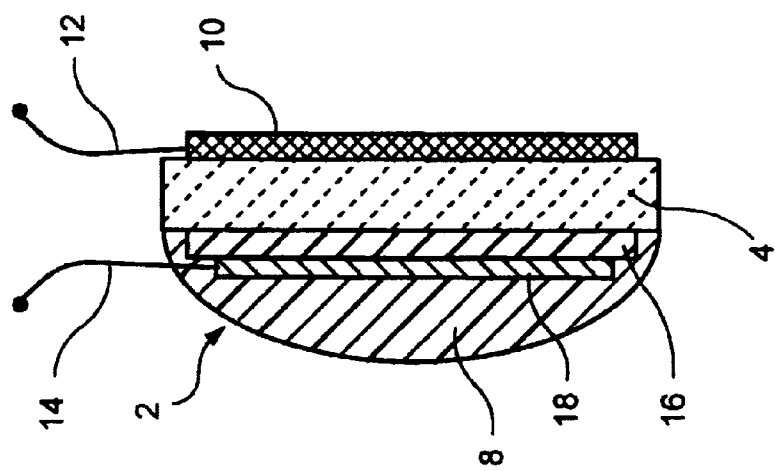
FIGS. 5 to 8 illustrate further example embodiments of the sensor according to the present invention.

In place of a silver layer 6 (FIGS. 1, 2), it is also possible to use any other silver compound as reference electrode. A corresponding construction according to the present invention is illustrated in FIG. 6. The structure is similar to the example embodiment illustrated in FIG. 1, except that the sensor component 2 is configured so that the silver layer 6 is replaced by a layer 16 of a silver compound 16, e.g., of silver sulphide (AgS), and, on top of this, an electrode 18, e.g., consisting of gold or another metal, provided with the lead 14.

However, it is possible for the silver layer 6 as illustrated in FIG. 1 or the silver compound 16 as illustrated in FIG. 6 to be omitted entirely if a liquid having a known concentration of sulphur compounds is used as reference. In this case, the difference in the electro-chemical potentials of the liquid to be analyzed and the reference liquid is measured, with the potential of the reference liquid remaining constant.

Figure 7:
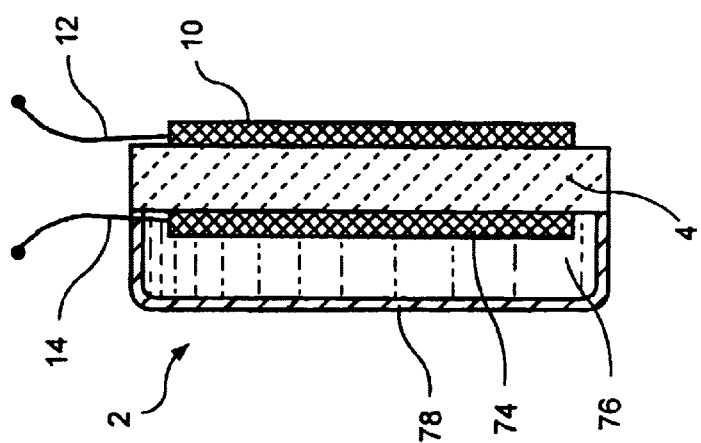

An example of this arrangement is illustrated in FIG. 7. The sensor component 2 has a similar structure to that illustrated in FIG. 1. However, the reference electrode 74 located on the side away from the liquid to be measured does not include silver or a silver compound but consists of any other metal, e.g., gold, and is porous. Over it there is a chamber 76 which is filled with a sulphurcontaining reference liquid. A cover 78 is present so that the reference liquid does not come into contact with the liquid to be measured. The reference liquid may be a liquid having a defined concentration of sulphur compounds. However, a liquid or a gel or a solid having a defined silver or sulphur activity may also be present in the chamber 76. A gaseous reference may also be introduced into the chamber 76, but the cover 78 may be made be not only liquid-tight but also gas tight, which may place greater technical demands on the construction, and may lead to increased costs.

It may be seen from equation (1) that it may be advantageous for the sensor component to be provided with a temperature sensor. This may be, for example, a thermocouple, a resistance thermometer or a semiconductor temperature sensor.

It is also possible to heat the sensor component in a controlled or regulated fashion to a particular working temperature. Especially in cases in which the temperature of the liquid the concentration of sulphur compounds of which is to be detected changes frequently, as is the case, for example, for the fuel of a motor vehicle, the sensor component may be heated. If the ionic conductivity of the thermally activated membrane is too low, the internal electrical resistance of the membrane becomes too great, so that the sensor signal may no longer be read reliably. Particularly in the case of very low temperatures, as may occur, for example, in winter operation of a motor vehicle, the ionic conductivity in unheated use may be too low for the sensor to be operated reliably.

Figure 8:
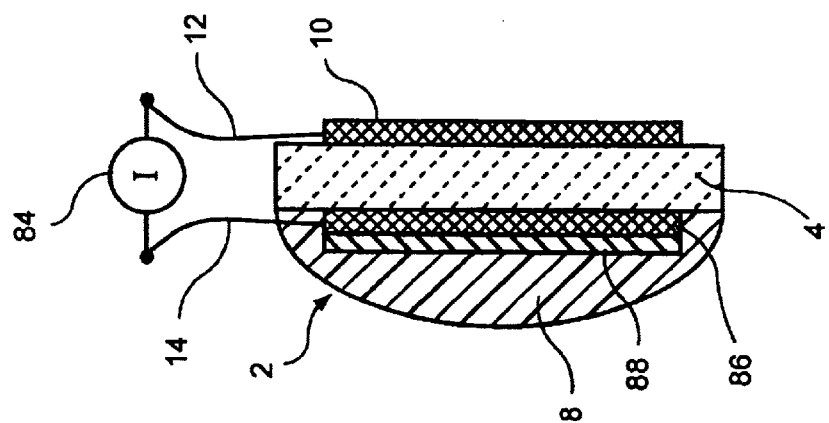

Furthermore, the sensor according to the present invention may be constructed according to the amperometric principle. FIG. 8 illustrates how such a sensor component operating according to the amperometric principle may be constructed. Porous electrodes 10 and 86 which are connected to the leads 12 and 14 are applied on the two sides of a membrane 4 which conducts silver ions. On the side which is covered by the covering composition 8 and faces away from the liquid to be analyzed, there is an additional layer 88 of a silversulphur compound, e.g., of AgS. Also possible is an example embodiment in which the layer 88 is in direct contact with the membrane 4. Due to the above described electromotor force developed, short-circuiting the sensor via a current measuring instrument 84, may result in a current which is a generally linear function of the concentration of sulphur compounds in the liquid to be analyzed. An AgS layer may then gradually be formed on that side of the sensor component 2 which is facing the liquid. As long as the AgS layer remains porous, it does not interfere with the function of the sensor. This construction is particularly suitable for low sulphur concentrations since in such cases the current is low and it accordingly takes a long time for the side in contact with the liquid to be coated with AgS.

The presence of a third electrode on the membrane (located, in particular, on the surface facing the liquid to be analyzed) and connected via a voltage source to the electrode facing the liquid stabilizes the potential of the electrode facing the liquid and has a positive effect on the stability of the sensor signal and on its sensitivity.

German Published Patent Application No. 198 45 397 describes disposing in the fuel an adsorber which desulphurizes the fuel. Depending on the concentration of sulphur compounds in the fuel, a single sensor according to the present invention may be used to determine this concentration in the fuel and thus, by an integration method, to determine the loading stage of a sulphur adsorber.

To determine the amount of sulphur stored in an NOx trap, the sulphur content in the fuel is determined by the sensor according to the present invention. The amount of sulphur introduced into the NOx trap by the exhaust gas may be calculated from the mass flow of fuel. This amount of sulphur introduced into the NOx trap by the exhaust gas may be calculated from the mass flow of fuel. This amount of sulphur introduced into the NOx trap per unit time is accumulated and compared with a permissible value. If the permissible value is exceeded, this signals that desulphating is necessary. In a further development, additional boundary conditions may also be incorporated in the cumulation of the amount of sulphur stored per unit time in the NOx trap. Thus, for example, the air ratio, the temperature of the NOx trap with sulphur may be taken into account. This cumulation of the amount of sulphur stored per unit time in the NOx trap represents a more precise variant, but is also significantly more costly to apply.

The sensor component according to the present invention may also be used for switching in a desulphurisation device only when an excessive sulphur concentration is measured in the fuel, thus increasing the life of the NOx trap.

Figure 9:
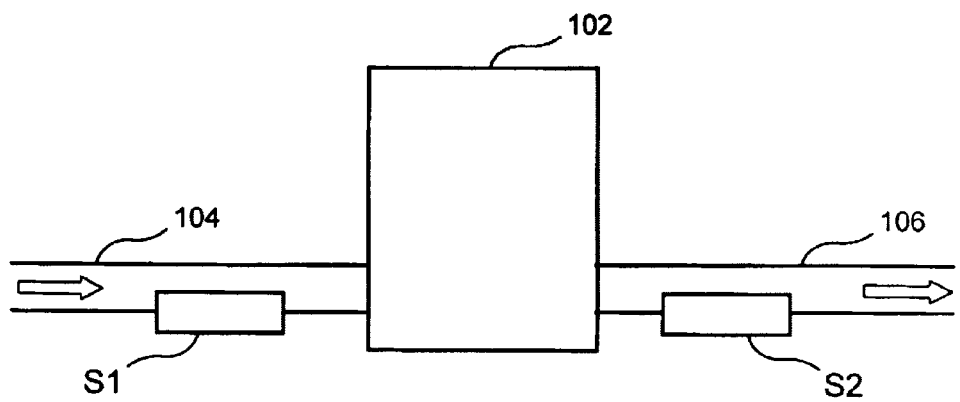
FIGS. 9 and 10 illustrate example embodiments of applications of a sensor according to the present invention.

FIG. 9 illustrates a further application of the sensor according to the present invention. The sulphur adsorber 102 is provided with an inlet line 104 and an outlet line 106. Both the inlet line 104 and the outlet line 106 are each provided with a sensor component S1 and S2 according to the present invention which each generate a sensor output signal. Comparison of the two signals, e.g., the difference between them, then enables a conclusion to be drawn as to the degree of loading and the remaining sulphur removal capacity of the sulphur adsorber 102. Sensor component S1 then indicates the concentration of sulphur compounds in the fuel, and sensor component S2 indicates the value for the fuel, from which the sulphur has been removed.

In a further example embodiment, a sensor may be configured so that its reference electrode is in contact with the untreated fuel in the fuel tank of the vehicle. In this case, the fuel acts as the reference material. Such a sensor is similar to the example embodiment illustrated in FIG. 7, but the closed compartment 78 (FIG. 7) is replaced by the fuel tank. In the case of the example embodiment illustrated in FIG. 9, the reference electrode of the sensor S2 may, for example, be exposed directly to the fuel from the fuel tank.

Figure 10:
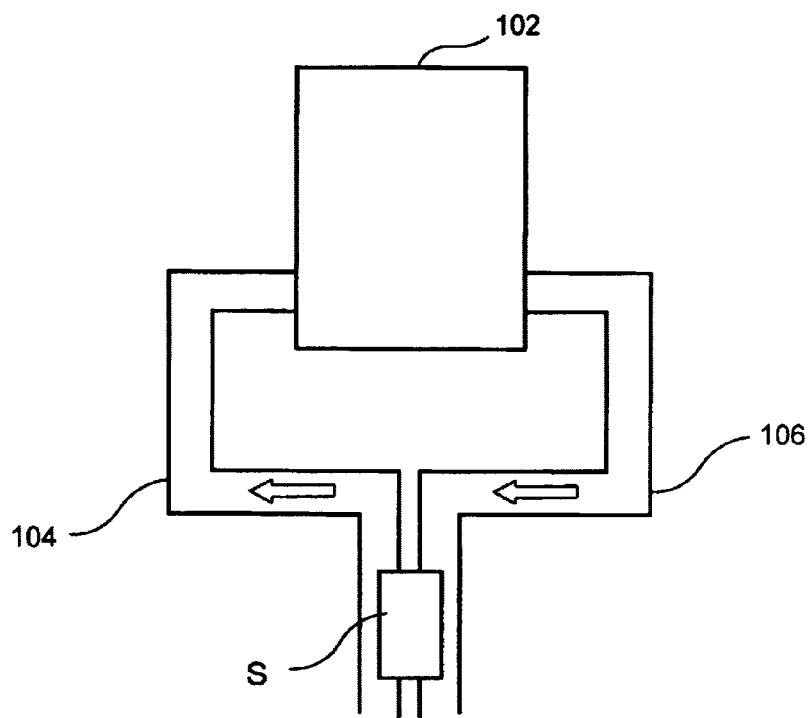

A particularly elegant example embodiment is illustrated in FIG. 10. The inlet line 104 and the outlet line 106 are arranged so that each side of the sensor component S is in contact with one side. In this case, the component may in the simplest case consist of only the membrane which conducts silver ions and on each side a porous electrode (e.g., of gold). The voltage to be measured provides a measure of the ratio of the concentration of sulphur compounds before and after the adsorber 102. If the output voltage of the sensor is zero, there is no longer a difference in the concentration of sulphur compounds in the two liquids, i.e., the sulphur adsorber 102 is exhausted.

An additional sensor constructed according to the present invention, as illustrated, for example, in FIGS. 1 to 8, which is installed at any point in the tank or in the inlet line 104 or in the outlet line 106 may be employed for feasibility studies and as an alarm device.

What is claimed is:

1. A sensor for determining a concentration of sulphur compounds in a liquid, comprising:
   a working electrode in contact with the liquid;
   a reference electrode insulated from the liquid;
   a liquid-impermeable membrane located between the working electrode and the reference electrode and permeable to an ion that forms a chemical compound with the sulphur compounds in the liquid; and
   a reference material that is one of in contact with the reference electrode and arranged to form the reference electrode;
   wherein the liquid includes a fuel.

2. The sensor according to claim 1, wherein
   the reference material includes an ion that is identical to the ion to which the membrane is permeable; or
   the reference material is oxidizable to an ion that is identical to the ion to which the membrane is permeable.

3. The sensor according to claim 2, wherein the reference material includes one of silver and a silver-containing compound.

4. The sensor according to claim 3, wherein the membrane includes a silver ion conductor.

5. The sensor according to claim 4, wherein the silver ion conductor includes at least one of Ag-$\beta''$-$Al_2O_3$, Ag-$\beta$-$Al_2O_3$, AgCl and AgI.

6. The sensor according to claim 2, wherein the reference material includes gold.

7. The sensor according to claim 1, wherein the reference material includes a sulphur-containing material.

8. The sensor according to claim 7, wherein the reference material includes a liquid having a defined sulphur content.

9. The sensor according to claim 1, wherein the sensor is configured for measurement according to one of a potentiometric principle and an amperometric principle.

10. The sensor according to claim 1, wherein the sensor is coated with an insulating material so that only the working electrode is in contact with the liquid.

11. The sensor according to claim 1, further comprising a third electrode connected via a voltage source to the working electrode and located on the membrane.

12. The sensor according to claim 1, wherein the fuel includes at least one of petrol, diesel fuel, fuel oil, liquified gas, methanol and ethanol.

13. The sensor according to claim 1, further comprising:
a temperature sensor to sense a temperature of the liquid.

14. The sensor according to claim 13, wherein the temperature sensor includes one of a thermocouple, a resistance thermometer, and a semiconductor temperature sensor.

15. The sensor according to claim 1, further comprising:
a heating arrangement to regulate a temperature of the sensor.

16. An apparatus for determining a degree of loading of sulphur adsorber installed in a fuel line, comprising:
a first sensor arranged before the adsorber; and
a second sensor arranged after the adsorber;
wherein each of the first sensor and the second sensor is configured to determine a concentration of sulphur compounds in a liquid, each of the first sensor and the second sensor including:
a working electrode in contact with the liquid;
a reference electrode insulated from the liquid;
a liquid-impermeable membrane located between the working electrode and the reference electrode and permeable to an ion that forms a chemical compound with the sulphur compounds in the liquid; and
a reference material that is one of in contact with the reference electrode and arranged to form the reference electrode; and
wherein the apparatus is configured to determine the degree of loading of the sulphur adsorber in accordance with a comparison of output signals of the first sensor and the second sensor.

17. The apparatus according to claim 16, wherein the reference electrode of the second sensor is in contact with untreated fuel before the adsorber.

18. An apparatus for determining a degree of loading of a sulphur adsorber installed in a fuel line, comprising:
a sensor configured to determine a concentration of sulphur compounds in a liquid, the sensor including:
a working electrode in contact with the liquid;
a reference electrode insulated from the liquid;
a liquid-impermeable membrane located between the working electrode and the reference electrode and permeable to an ion that forms a chemical compound with the sulphur compounds in the liquid; and
a reference material that is one of in contact with the reference electrode and arranged to form the reference electrode;
wherein the working electrode is in contact with the fuel before the adsorber and the reference electrode is in contact with the fuel after the adsorber.

19. A method for determining the degree of sulphur loading of an Nox trap arranged in an exhaust gas purification system of a 4-stroke engine that is run lean, comprising the step of providing a sensor configured to determine a concentration of sulphur compounds in a liquid, the sensor including:
a working electrode in contact with the liquid;
a reference electrode insulated from the liquid;
a liquid-impermeable membrane located between the working electrode and the reference electrode and permeable to an ion that forms a chemical compound with the sulphur compounds in the liquid; and
a reference material that is one of in contact with the reference electrode and arranged to form the reference electrode;
wherein the liquid includes a fuel.

* * * * *